United States Patent [19]
Marrelli et al.

[11] Patent Number: 5,673,026
[45] Date of Patent: Sep. 30, 1997

[54] STOPPED FLOW DETECTION USING STATISTICAL METHODS

[75] Inventors: John David Marrelli, Houston; Farhan Siddiqui, Katy, both of Tex.

[73] Assignee: Texaco Inc., White Plains, N.Y.

[21] Appl. No.: 260,288

[22] Filed: Jun. 14, 1994

[51] Int. Cl.[6] ................................................. G08B 21/00
[52] U.S. Cl. ..................... 340/608; 340/618; 340/621; 73/661.18; 73/61.44; 324/637; 324/639
[58] Field of Search .................................. 340/608, 618, 340/621; 73/61.43, 323, 861.18, 340, 61.44; 324/640, 637, 639

[56] References Cited

U.S. PATENT DOCUMENTS

| | | | |
|---|---|---|---|
| 2,698,929 | 1/1955 | Greacen, 3rd et al. | 340/239 |
| 3,366,942 | 1/1968 | Deane | 340/608 |
| 5,299,594 | 4/1994 | Lord et al. | 137/101.19 |
| 5,351,036 | 9/1994 | Brown et al. | 340/618 |

OTHER PUBLICATIONS

Statistics for Experimentalists, Cooper, Atlas Computer Laboratory Chilton, Didcot, Bershire.

*Primary Examiner*—Brent A. Swarthout
*Assistant Examiner*—Julie B. Lieu
*Attorney, Agent, or Firm*—Henry H. Gibson; William J. Beard

[57] ABSTRACT

A method for determining a stopped flow condition in a fluid fraction measuring apparatus includes the steps of establishing a minimum threshold level of statistical variation in the measured parameter repetitively (continuously) monitored by the measuring apparatus, and giving an indication when the standard deviation, statistical average, or the kurtosis of the measured parameter or characteristic drops to the threshold level.

6 Claims, 2 Drawing Sheets

STOPPED FLOW DETECTION USING STATISTICAL METHODS

BACKGROUND OF THE INVENTION

1. The Field of the Invention

The present invention relates to a method for determining flow conditions in a pipe, and in particular a side flow sampling pipe which is usually of considerably smaller diameter than the main flow pipe, by utilizing the inherent variation in flowing fluid as an indicator of flow/no flow conditions.

2. The Prior Art

It has not always been possible to tell if there was really a flow condition in a pipe, especially when there was the possibility that normal flow would cause a stoppage of flow due, for example, to build-up of deposits within the pipe. This is particularly true in situations in which a side flow sampling technique is used to monitor and/or control a primary flow. Usually the side flow sampling device will utilize pipes of considerably smaller diameter than the main flow and thus more prone to clogging than the primary flow. A stopped flow in the sampling device could indicate that a similar problem is developing in the primary flow requiring remedial efforts for correction. Continuing to treat a system as being in a flow condition, when there actually is no flow, clearly can lead to major operation problems, such as equipment failure and loss of production.

The present invention was developed specifically to avoid anticipated problems in the monitoring of high paraffin, low pour-point fluids, such as those found in Indonesia and China.

SUMMARY OF THE INVENTION

The present invention utilizes a method using the inherent variation in flowing fluids, even totally clean single phase fluid, as an indicator of flow/no flow conditions. The present invention provides an error check against reading stationary blockage as continuing production of oil or water by first establishing a minimum threshold reading and then monitoring the reading and giving an indication and/or alarm should the measured reading drop below the threshold.

BRIEF DESCRIPTION OF THE DRAWINGS

The present invention will now be described, by way of example, with reference to the accompanying drawings, in which.

DETAILED DESCRIPTION OF THE PREFERRED EMBODIMENT

Figure 1:
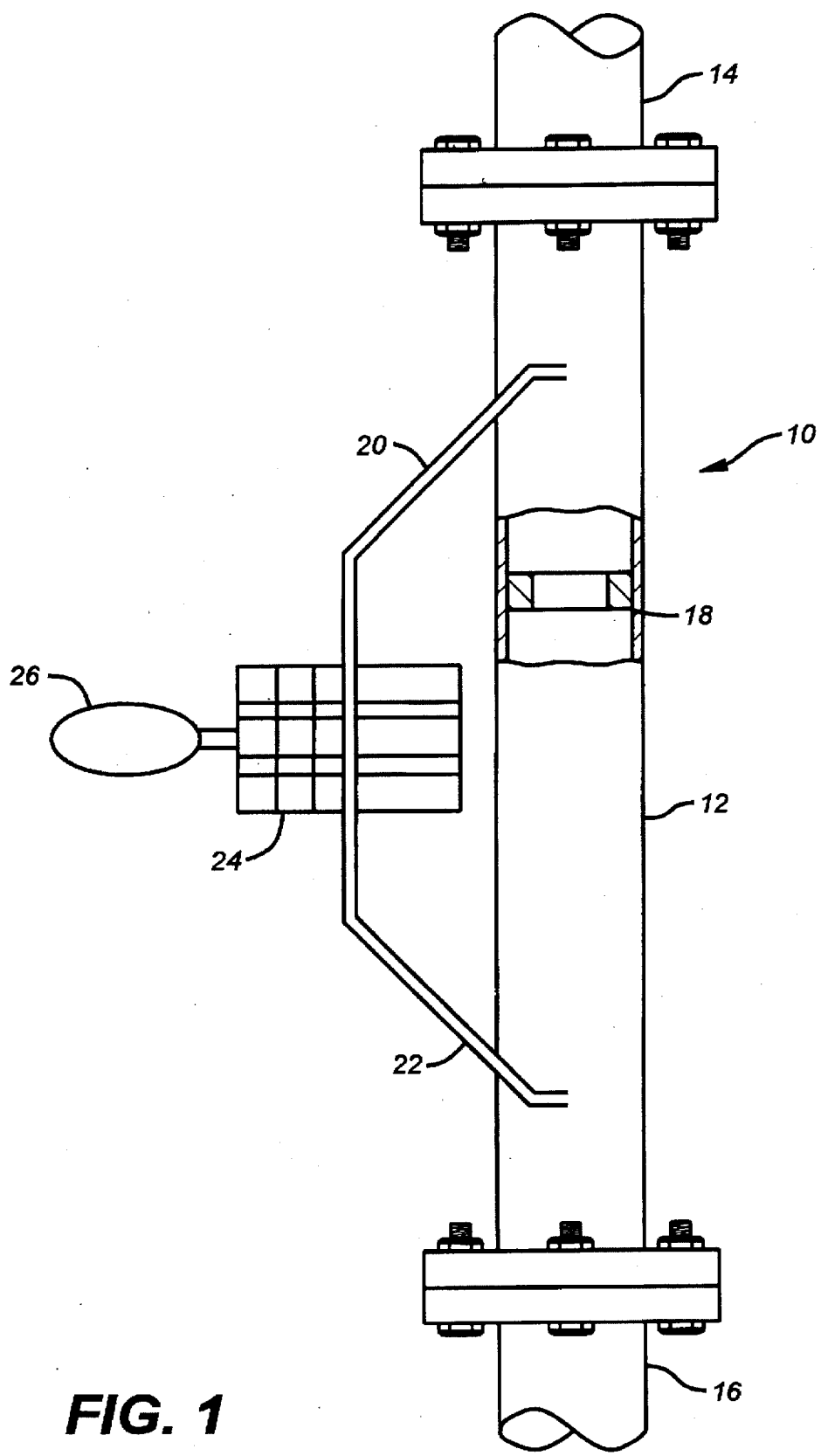
FIG. 1 is a schematic representation of a side stream sampling device of the general type which would benefit from the present invention.

A known side stream sampling device 10 is shown in FIG. 1 and is along the lines of the water cut monitor described in U.S. Pat. No. 5,001,434, the disclosure of which is incorporated herein by reference. The device includes a large diameter pipe segment 12 mounted between like large diameter primary flow pipes 14, 16 of a fluid distribution system (not shown). A flow restriction means 18, such as the illustrated orifice plate 18, is fixed in pipe segment 12 intermediate the ends thereof. First and second sampling tubes 20, 22, both of which have a smaller diameters than pipe segment 12 or pipes 14, 16, each have one end opening into pipe segment 12, on opposite sides of the flow restriction means, and their opposite ends opening into opposite sides of test cell 24. The purpose of the flow restriction is to assure that at least some of the primary flow will pass through the side stream sampling device. Both sampling tubes 20, 22 can be provided with valve means (not shown) to isolate the test cell. The test cell 24 can be of known type, such as that described in U.S. Pat. No. 4,947,127, the disclosure of which is also incorporated herein by reference. The test cell preferably provides for sample and reference microwaves and includes a temperature transducer 26. It is to be understood that this drawing is extremely simplified and that many conventional things, such as the above mentioned valves, have not been illustrated for sake of simplicity in the drawings but would be understood by those skilled in the art.

The device 10 extracts a small sample stream of fluid from the main line on one side, upstream, of the flow restriction 18, passes it through the sensor cell 24 and then returns it to the main line on the opposite side, downstream, of the flow restrictor 18. The velocity of the flow through the sensor cell 24 is governed by the size and type of flow restrictor 18 in the main line and the diameter $d_s$ of the sensor cell piping 20, 22.

Many field applications concern fluids which, because of their composition, can cause blockage of the side stream flow. These fluids may contain, for example, particulate matter or paraffins which are solid at some temperature of normal operating conditions. To demonstrate that plugging will occur, it is only necessary to know that the following general equations are monotonic. Exact values of coefficients and exponents control duration to plugging, once flow is reduced below a critical flow rate for existing conditions.

Figure 2A:
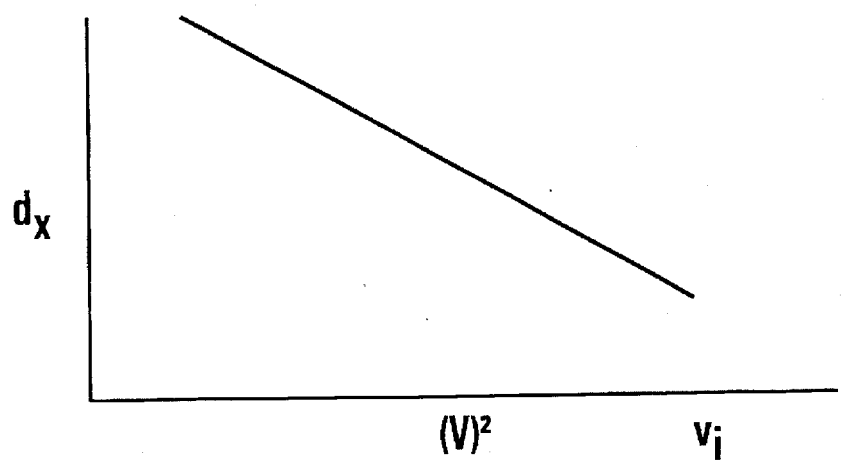
FIGS. 2A to 2C show graphs useful in explaining the present invention.

Studies have demonstrated inverse monotonic shear rate dependency of wax deposition of a general mathematical form as shown in FIG. 2A and by the following equation:

$$d_x = K * V^{-2} + V_o$$

Figure 2B:
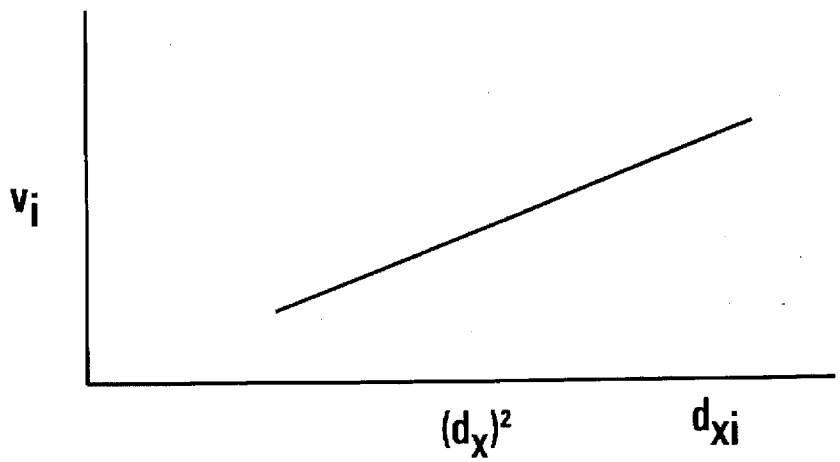

Deposition of a waxy layer of thickness $d_x$ at flow velocity v would likely lead to plugging. Shear rate is a monotonic function of linear flow velocity. Common sense indicates most types of plugging will follow similar functional forms with shear rate. Because of the "in parallel" action of the main line (modelled using pipe phase), any reduction of sensor cell flow line effective diameter will cause the shear rate (or velocity) to drop in the sensor cell according to general function form of FIG. 2B.

$$V = K_2 \frac{1}{d_x^2}$$

Figure 2C:
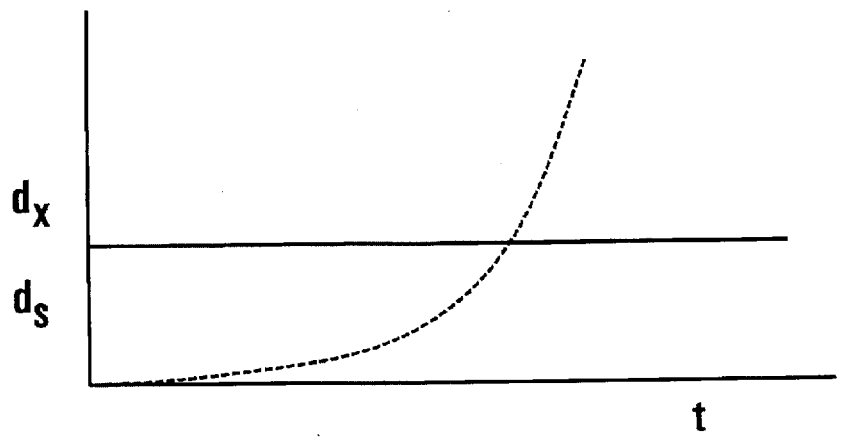

The effect of reducing the sensor cell flow rate would be (in a positive feedback way) to accelerate any tendencies to plug. Furthermore, during shut down, in cases of waxy-fluids, solid paraffin is likely to form having a diameter $d_x$ greater than $d_s$ thereby plugging the flow, FIG. 2C.

$$d_x e^{(d_x)/t}$$

In order to effect a restart, it is necessary to know when side stream flow has resumed, after application of heat to the side stream piping by methods such as electrical tracing or juxtaposition to the main pipeline. By virtue of the design described above, removal of the blockage is expected to be abrupt as fluid velocity increases with decreasing blockage. It is essential for unmanned sites to detect and report blockage conditions which have to be cleared for any subsequent data to be meaningful.

A stopped flow condition is distinguished from the flowing condition using either the standard deviation of the phase shift or the standard deviation of the attenuation of the microwave energy passing through the microwave sensor.

When standard deviation of one or both of these variables falls below a criterion value, stopped flow is indicated. Operators are sent a negative value over the current loop outputs, which will definitely alert them to a critical condition requiring attention.

The statistical average, standard deviation and kurtosis and the first, second and third moments of the data comprising the set of all measurements in a set time period, for example from 0.25 seconds to 60 seconds. These statistical measures are commonly known and need little discussion. These measurements are collected on the phase shift and attenuation of microwaves passing through the fluids passing through a microwave sensor of a water cut monitor, such as the one described in U.S. Pat. No. 4,947,127, the disclosure of which is incorporated herein by reference. Reference is also made to U.S. Pat. Nos. 4,660,414, which shows sampling using inclined piping; 4,499,418, which also shows a water cut monitor; and 4,764,718, which shows the two curve concept. Each of these disclosures is also incorporated herein by reference.

Average data is normally used to predict water cut, as described in many publications, such as "Continuous Determination of Oil Pipeline Watercut, Salinity, and API Gravity Regardless of Gas Fraction: The Microwave Watercut Monitor" by J. D. Marrelli et al presented at the SPE International Meeting, Bejing, China Mar. 24–27, 1992 (SPE 22401). Standard deviation is a measure of the deviation from the average value of a data set. If the data is normally or Gaussian distributed about 68% of the data set falls within one standard deviation of the average value. The kurtosis, or deviation from normality, is used to determine if the data is "normally distributed" or Gaussian in the statistical sense. Low kurtosis indicates that the normality assumption is valid.

Inhomogeneities in the fluids during flow cause a large increase in standard deviation during flow, but only a small change in the kurtosis or the average. The standard deviation of the resulting data is described as the deviation of data around the average.

In the current invention, the monitor 10, including its internal microprocess constantly searches for the lowest standard deviation of phase shift and attenuation during operation, which includes stopped flow due to deliberate shutting of the valve to the monitor side stream sample. These low values are retained during operation and are compared to running values of standard deviation. When standard deviation values fall to within 25% of the lowest value of standard deviation a signal is issued as an alarm to the operator which indicates a stopped flow situation needing correction. The present invention is intended for use with known apparatus and could be used to initiate corrective procedures. First an indication of the stopped flow condition would be given, such as an alarm, and the corrective action taken, such as injecting a solvent into the flow line of activating heaters depending on the expected cause of the flow stoppage.

The flow stoppage could also be caused by a stopped up sensor or a bad pressure cell. Either case would cause the pressure drop across the flow restrictor to drop and any deviation in this drop would indicate a stoppage.

The present invention may be subject to many modifications and changes which will be apparent to those skilled in the art. The present embodiment is therefor intended in all respects as being illustrative and not restrictive of the scope of the present invention as define by the appended claims.

We claim:

1. In conjunction with a fluid fraction measuring means capable of measuring a physical flow characteristic, a method to determine stopped flow conditions comprising the steps of:

establishing a minimum threshold level reading of the statistical variation of a physical flow characteristic measured by said measuring means;

continuously monitoring readings of the statistical variation of said physical flow characteristic measured by said measuring means;

giving an indication of stopped flow when the reading of the statistical variation of said physical flow characteristic measured by said measuring means drops to said threshold level.

2. The method according to claim 1 wherein the minimum threshold is set at a statistical variation of said flow characteristic representative of a stopped flow condition.

3. A method to determine a stopped flow condition in a pipe line having microwave sensor and transmitter means disposed therein, said method comprising the steps of:

applying microwave energy to the fluid passing through said sensor means; and determining either the standard deviation of the phase shift or the standard deviation of the attenuation of the microwave energy passing through said microwave sensor to distinguish a flowing condition from a stopped flow condition, as indicated by one or both of these statistical variables falling below a predetermined criterion value.

4. The method according to claim 3 further comprising:

sending pipeline operators an alarm to alert them to a critical condition requiring attention.

5. The method according to claim 3 further comprising the step of:

determining the statistical average, standard deviation and kurtosis and the First, Second, and Third moments of the data comprising all measurements made by said sensor means in a set time period.

6. The method according to claim 5 wherein the set time period is in a range of from 0.25 seconds to 60 seconds.

* * * * *